United States Patent [19]

Kocal

[11] Patent Number: 5,344,997
[45] Date of Patent: * Sep. 6, 1994

[54] ALKYLATION OF AROMATICS USING A FLUORIDED SILICA-ALUMINA CATALYST

[75] Inventor: Joseph A. Kocal, Gurnee, Ill.

[73] Assignee: UOP, Des Plaines, Ill.

[*] Notice: The portion of the term of this patent subsequent to Mar. 23, 2010 has been disclaimed.

[21] Appl. No.: 989,858

[22] Filed: Dec. 14, 1992

Related U.S. Application Data

[63] Continuation-in-part of Ser. No. 816,341, Dec. 23, 1991, Pat. No. 5,196,574.

[51] Int. Cl.$^5$ .................. C07C 39/12; C07C 37/00; C07C 2/64; C07C 15/107; C07C 41/00; C07C 2/66; C07C 2/70; C07C 2/68

[52] U.S. Cl. .................. 568/628; 585/455; 585/456; 585/462; 585/463; 585/467; 585/468; 252/553; 252/556; 252/558; 568/631; 568/632; 568/658; 568/731; 568/732; 568/734; 568/736; 568/766; 568/780; 568/781; 568/785; 568/790; 568/804; 562/79; 562/82; 562/88; 562/91; 562/94; 562/95; 562/99

[58] Field of Search .............. 585/455, 456, 462, 463, 585/467, 468; 252/553, 556, 558; 562/94, 79, 82, 88, 91, 95, 99; 568/628, 631, 632, 658, 731, 732, 734, 736, 766, 780, 781, 785, 790, 804; 554/89, 98

[56] References Cited

U.S. PATENT DOCUMENTS 2,620,314 12/1952 Hoekstra .
3,169,999 2/1965 Erickson et al. .
3,201,487 8/1965 Kovsch et al. .
4,301,316 11/1981 Young .
4,301,317 11/1981 Young .
4,358,628 11/1982 Slaugh .
4,870,222 9/1989 Bakas et al. .
5,196,574 3/1993 Kocal .................. 585/455

FOREIGN PATENT DOCUMENTS 0160145 11/1985 European Pat. Off. .
2237641-A 9/1990 Japan .

OTHER PUBLICATIONS

Kurosaki and Okazaki, *Bull. Chem. Soc., Japan*, 63,2363 (1990).
Kurosaki and Okazaki, *Chemistry Letters*, 589 (1991).
R. A. Myers, "Petroleum Refining Processes", 4–36 to 4–38 (McGraw-Hill Book Company), 1986.

*Primary Examiner*—Helen M. S. Sneed
*Assistant Examiner*—E. D. Irzinski
*Attorney, Agent, or Firm*—Thomas K. McBride; Eugene I. Snyder

[57] ABSTRACT

A fluorided silica-alumina catalyst, particularly one with a silica:alumina ratio in the range of 1:1–9:1 containing from 1 to 6 weight percent fluoride, is particularly effective in the liquid phase alkylation of benzene by linear olefins to produce linear alkyl benzenes at temperatures no greater than 140° C. These catalysts also are effective in the liquid phase alkylation of alkylatable aromatics generally with a variety of alkylating agents, including olefins, alcohols, and alkyl halides.

11 Claims, No Drawings

ALKYLATION OF AROMATICS USING A FLUORIDED SILICA-ALUMINA CATALYST

CROSS REFERENCE To RELATED APPLICATION

This application is a continuation-in-part of my copending application, Ser. No. 07/816,341, filed Dec. 23, 1991, and now U.S. Pat. No. 5,196,574 all of which is hereby incorporated by reference.

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates as initially prepared had substantial branching in the alkyl chain. This situation was maintained until the early 1960's when it became apparent that the branched alkyl-based detergents were contributing to the pollution of lakes and streams and forming relatively stable foams. Examination of the problem showed that the branched structure of the alkyl chains was not susceptible to rapid biodegradation and the surfactant properties of the detergent thus persisted for long periods of time. This was not the case earlier when natural soaps were used, because of the rapid biodegradation of the linear chains in natural soaps.

After recognizing the biodegradability of ABS based on alkylation by linear olefins, industry turned its attention to the production of these unbranched olefins and their subsequent use in the production of linear alkyl benzenes. Processes were developed for efficient alkylation of benzene by available feedstocks containing linear olefins, and the production of linear alkyl benzenes (LAB) became another reliable process broadly available to the petroleum and petrochemical industry. It gradually evolved that HF-catalyzed alkylation was particularly effective in LAB production, and an HF-based alkylation process became the industry standard.

With increasing environmental concern came increasing disenchantment with HF as a catalyst and a concomitant need to find a substitute equal or superior to it in all respects. As regards criteria in addition to the price, the extent of conversion effected by the catalyst, the selectivity of monoalkylbenzene formation, and the linearity of alkylbenzenes produced loomed large. At this point the definition of several terms are necessary to adequately understand and appreciate what follows.

Alkylation typically is performed using an excess of benzene relative to olefins. The ideal catalyst would show 100% conversion of olefins using an equal molar proportion of benzene and olefins, but since this is not attained one strives for maximum olefin conversion using a benzene to olefin molar ratio up to about 30. The better the catalyst, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio).

The degree of conversion may be expressed by the formula, $$V = \frac{C}{T} \times 100,$$

where V equals percent conversion, C equals moles of olefin consumed, and T equals moles olefin initially present.

However active the catalyst may be, it is not valuable unless it also is selective. Selectivity is defined as the percentage of total olefin consumed under reaction conditions which appears as monoalkylbenzene and can be expressed by the equation, $$S = \frac{M}{C} \times 100,$$

where S equals selectivity, M equals moles of monoalkylbenzenes produced, and C equals moles olefin consumed. The better the selectivity, the more desirable is the catalyst. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S >85%) the results calculated from the two equations are nearly identical. The latter of the foregoing two equations is routinely used in commercial practice because of the difficulty in distinguishing between oligomers and polyalkylbenzenes.

Finally, the reaction of linear olefins with benzene in principal proceeds according to the equation,

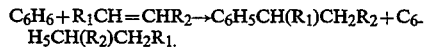

$C_6H_6+R_1CH=CHR_2 \rightarrow C_6H_5CH(R_1)CH_2R_2+C_6H_5CH(R_2)CH_2R_1$.

Note that the side chain is branched solely at the benzylic carbon and contains only one branch in the chain. Although strictly speaking this is not a linear alkylbenzene, nonetheless the terminology which has grown up around the process and product in fact includes as linear alkylbenzenes those materials whose alkyl group chemically arises directly from linear olefins and therefore includes alpha-branched olefins. Because alkylation catalysts also may induce the rearrangement of olefins to give products which are not readily biodegradable (vide supra), for example, α,α-disubstituted olefins which subsequently react with benzene to afford an alkyl benzene with branching at other than the benzylic carbon,

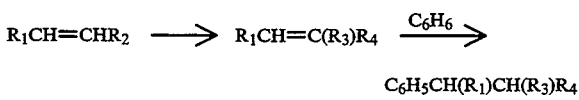

$R_1CH=CHR_2 \longrightarrow R_1CH=C(R_3)R_4 \xrightarrow{C_6H_6}$ $C_6H_5CH(R_1)CH(R_3)R_4$ the degree to which the catalyst effects formation of linear alkyl benzenes is another important catalyst parameter. The degree of linearity can be expressed by the equation, $$D = \frac{L}{M} \times 100,$$

where D equals degree of linearity, L equals moles of linear monoalkyl benzene produced, and M equals moles of monoalkyl benzene produced.

Consequently, the ideal catalyst is one where V equals 100, S equals 100, and D equals 100. The minimum requirement is that linearity be at least 90% at a selectivity of at least 85% and at a conversion of at least 98%. These are minimum requirements; that is, if a catalyst fails to meet all of the foregoing requirements simultaneously the catalyst is commercially unacceptable.

The linearity requirement is assuming added importance and significance in view of the expectation in some areas of minimum standards for linearity in detergents of 92–95% near-term, increasing to 95–98% by about the year 2000. Since the olefinic feedstock used for alkylation generally contains a small percentage of non-linear olefins—a non-liner olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

Our solution to the problem of identifying a catalyst for detergent alkylation which satisfies all the aforementioned criteria, and which in particular meets the increasingly stringent requirements of linearity, arose from our observation that the isomerization of linear olefins to non—linear olefins—this is the process ultimately responsible for non—linear detergent alkylate arising from a linear olefin feedstock—is quite sensitive to temperature but relatively insensitive to the particular candidate catalyst for the detergent alkylate process. This result was itself quite surprising, but more importantly it suggested that effecting alkylation at a lower temperature was the key to greater product linearity. Our focus then shifted to finding more active catalysts, i.e., materials which would catalyze detergent alkylation at lower temperatures.

The importance of our observation that temperature is the major factor in olefin isomerization and that the particular catalyst plays only a minor role cannot be overemphasized, for it permits one to focus solely on methods of reducing the alkylation temperature. Since the other requisites of a detergent alkylation process can be addressed in other ways, our observation significantly foreshortens the focus on ways to obtain an improved process. A result of our observation is the novel use of a solid acid catalyst to craft a new process permitting alkylation at a substantially lower temperature than that previously attainable using other members of this class of catalysts.

The use of silica-aluminas as a support for various metals in the alkylation of aromatics with olefins is reasonably well known. For example, U.S. Pat. No. 3,169,999 teaches a catalyst consisting essentially of small amounts of nickel and chromia on a silica-alumina support, and U.S. Pat. No. 3,201,487 teaches 25–50 weight percent chromia on a silica-alumina support, both for alkylation of aromatics by olefins. Crystalline aluminosilicates as catalysts in detergent alkylation has been described in U.S. Pat. No. 4,301,317 and 4,301,316.

U.S. Pat. No. 4,358,628 claims an alkylation process with an olefin using as a catalyst tungsten oxide supported on a porous silica-alumina support containing 70–90% silica prepared in a very particular way.

More relevant is European Patent Application 0160145 which teaches as a catalyst in detergent alkylation an amorphous silica-alumina having specified channels or networks of pores and with at least 10% of the cationic sites occupied by ions other than alkali or alkaline earth metals. Even more relevant is U.S. Pat. No. 4,870,222 where the patentees teach that amorphous silica-alumina is the most preferred catalyst for alkylation in a process for the production of a monoalkylated aromatic compound in which an aromatic is first alkylated, the product mixture is separated, and the polyalkylated material thereafter is transalkylated.

There appears to be few references to fluorided silica-aluminas in the literature. Japanese patent application J02237641-A refers to a silica-alumina (20% silica) which was contacted at 400° C. with $CCIF_3$ to afford a catalyst containing 28% fluorine as having a higher activity and a longer operating life in cumeme production by vapor phase alkylation of benzene. Kurosaki and Okazaki [Bull Chem. Soc. Japan, 63, 2363 (1990)] describe a silica:alumina (6.7:1) modified by vapor-phase fluorination with $CCIF_3$ at 350°–550° C. in the vapor phase alkylation of benzene with propylene. Cf. Kurosaki and Okazaki, Chemistry Letters, 589 (1991). However, in none of the prior art is there recognition of the benefits of a fluorided silica-alumina to afford higher linearity in the products resulting from the detergent alkylation process, especially as to a silica-alumina prepared by the method described within and containing the fluorine levels which we have found effective, nor is there recognition of the benefits of a fluorided silica-alumina in liquid phase alkylation generally.

SUMMARY OF THE INVENTION

The object of this invention is to prepare linear alkylbenzenes by the alkylation of benzene with an olefin, particularly in a continuous manner, where alkylation proceeds with at least 98% conversion of olefin, at least 85% selectivity of olefin conversion to monoalkylbenzenes, and with at least 90% linearity with respect to monoalkylbenzene formation. In an embodiment benzene in a total of from 5 to about 30 molar proportions is reacted with 1 molar proportion of a linear monoolefin, or a mixture of linear monoolefins, in the presence of a catalyst consisting essentially of a fluorided silica-alumina, where the weight ratio of silica to alumina is from about 1:1 to about 9:1. In a more specific embodiment the linear monoolefins have from 6 up to about 20 carbon atoms. In a still more specific embodiment the molar proportion of total benzene relative to total linear monoolefins is from about 8:1 to about 20:1. Other embodiments will be apparent from the ensuing description.

A broader object of this invention is a process for the liquid phase alkylation of aromatic compounds with a variety of alkylating agents using as a catalyst fluorided silica-aluminas, especially as prepared by fluoride impregnation. In a specific embodiment of this branch of our invention the alkylating agent is an olefin containing up to about 24 carbon atoms. In another embodiment the alkylating agent is an alcohol containing from 1 up to about 24 carbon atoms.

DESCRIPTION OF THE INVENTION

In our search for catalysts in a detergent alkylation process, and especially solid catalysts capable of being used as a bed in a continuous fixed bed detergent alkylation process, it soon became clear that the degree of branching in the alkyl chain of the resulting alkylbenzene (detergent alkylate) was principally a function of temperature, with lower reaction temperatures affording lower branching. Since linearity of the alkyl chain is an increasingly important environmental and regulatory consideration, our observation led to a search for catalysts which would effect alkylation in a continuous process at acceptable productivity rates and at a temperature not exceeding 140° C. For the purpose of this application an acceptable productivity means an olefin liquid hourly space velocity of at least 0.05 $hr^{-1}$. What we have found is that fluoridation of silica-aluminas affords a substantial activity increase over the non-fluorided material. As described in more detail within, silica-aluminas containing from 1 to 6 weight percent fluoride, calculated as fluorine, are quite suitable catalysts for a detergent alkylation process at temperatures not exceeding 140° C. and effect detergent alkylation with at least 98% conversion while simultaneously affording at least 85% selectivity to monoalkylbenzenes with at least 90% linearity of the alkyl side chain. Although our invention is particularly relevant to detergent alkylation, it is important to understand that our invention is generally applicable to the alkylation of alkylatable aromatic compounds with a large universe of alkylating agents, as will be clear from the material within.

The feedstocks containing the alkylating agent which are used in the practice of that branch of our invention applicable to detergent alkylation normally result from the dehydrogenation of paraffins. Since the entire dehydrogenation reaction mixture often is used, the reaction is not run to completion to minimize cracking, isomerization, and other undesirable and deleterious byproducts. The branched olefins which are formed are not removed, yet the total amount of nonlinear alkylbenzene formed still must be sufficiently small that the monoalkylate meets the requirements of 90% linearity. The polyolefins formed during dehydrogenation are minimized in the feedstocks used in the practice of this invention. Consequently the feedstocks are largely a mixture of unreacted paraffins and unbranched, linear monoolefins which typically are in the C6–C20 range, although those in the C8–C16 range are preferred in the practice of this invention, and those in the C10–C14 range are even more preferred. Unsaturation may appear anywhere on the linear monoolefin chain; there is no requirement as to the position of the double bond, but only a requirement as to the linearity of the olefin. See R. A. Myers, "Petroleum Refining Processes", 4-36 to 4-38. (McGraw-Hill Book Company), 1986.

In the broader case the alkylating agent is an olefin, an alcohol, or an alkyl halide containing from 1 up to about. 24 carbon atoms. Where the alkylating agent is an olefin the latter may be either branched or unbranched and also may be substituted with, for example, an aromatic substituent. Examples of suitable olefins include ethylene, propylene, the butenes, pentenes, hexenes, heptenes, octenes, nonenes, deceries, unclecertes, dodecenes, tridecenes, tetradecenes, pentadecenes, hexadecenes, heptadecenes, octadecenes, nonadeoenes, elcoseries, heneicosenes, docosenes, tricoseries, and tetracosenes. Further examples include styrene, phenylpropene, phenylbutene, phenylpentene, phenylhexene, and so forth.

Another class of alkylating agents which may be used in the practice of our invention are alcohols. Like the olefins, the alkyl chain in the alcohol may be branched or unbranched and the hydroxyl group may be found anywhere on the alkyl chain. That is, there is no particular requirement as to the spatial position of the hydroxyl moiety on the alkene chain. Examples of alcohols which may be successfully used in our invention include methanol, ethanol, propanol, butanol, pentanol, hexanol, heptanol, octanol, nonanol, decanol, undecanol, tetradecanol, and so forth. Especially relevant to this branch of the invention is methanol as the alcohol.

The last of the three classes of alkylating agents which may be frequently used in the practice of this invention are alkyl halides. Alkyl chlorides are probably the most widely used alkyl halides, but alkyl bromides also may be successfully used in the practice of our invention. As with alcohols, the paraffinic chain may be either branched or unbranched and the halogen may be found at any position along the chain. Suitable examples of alkyl halides include propyl chloride, propyl bromide, butyl chloride, butyl bromide, pentyl chloride, pentyl bromide, hexyl chloride, hexyl bromide, heptyl chloride, heptyl bromide, benzyl chloride, benzyl bromide, xylyl chloride, xylyl bromide, phenethyl chloride, phenethyl bromide, allyl chloride, allyl bromide, butenyl chloride, butenyl bromide, and so forth.

Where the process is detergent alkylation, the linear monoolefins in the feedstock are reacted with benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist of not only the desired monoalkylbenzenes, but would also contain large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene:linear monoolefin molar ratio of from 5:1 up to as high as 30:1 is recommended, although the process normally operates satisfactorily at a total benzene:linear monoolefins molar ratio between about 8:1 and about 20:1.

In the more general case the alkylating agent is reacted with an alkylatable aromatic compound. Such aromatic compounds are selected from the group consisting of benzene, naphthalene, anthracene, phenanthracene, and substituted derivatives thereof. The most important class of substituents are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds include benzene, naphthalene, anthracene, phenanthrene, biphenyl, toluene, xylene, ethylbenzene, phenol, anisole, propylbenzene, butylbenzene, pentylbenzene, hexylbenzene, heptylbenzene, octylbenzene, and so forth; anisole, ethoxy-, propoxy-, butoxy-, pentoxy-, hexoxybenzene, and so forth.

Where the process is detergent alkylation, the benzene and linear monoolefins in the $C_6$–$C_{20}$ range, are reacted in the presence of a catalyst under alkylation conditions. These alkylation conditions include a temperature in the range between about 60° C. and 175° C., most usually between about 70° C. and 150° C., and preferably in the range from 80° to 135° C. Since the alkylation is conducted as a liquid phase process, pressures must be sufficient to maintain the reactants in the liquid state. The requisite pressure necessarily depends upon the feedstock and temperature, but normally is in the range of 200–1000 psig (1379–6985 kPa), and most usually 300–500 psig (2069–3448 kPa).

In the more general case, there is a wide variation in the alkylation conditions of an alkylatable aromatic compound by an alkylating agent depending upon the reactivity of the two reactants. For example, for hydroxy benzenes (phenols) the hydroxyl moiety is found to be a quite activating group toward alkylation, and therefore the hydroxy benzenes are readily alkylated so that temperatures of no more than about 150° C. suffice. On the other hand, where the aromatic is an unsubstituted aromatic, such as benzene, and the alkylating agent is a lower olefin, such as propylene, temperatures as high as 400° C. may be necessary. Consequently, the temperature range appropriate for alkylation will be between about 60° and about 400° C., with the most usual temperature range being between 100° and 225° C. As regards pressures, since the alkylation is desirably conducted as a liquid phase process the reaction pressure must be sufficient to maintain the reactants in the liquid stage. This is the sole pressure requirement for the practice of this invention, and since a wide variety of alkylatable aromatics compounds and alkylating agents may be used in the practice of this invention it can be readily appreciated that there exists a wide variation in reaction pressure, from atmospheric up to as high as about 2000 pounds per square inch (14,000 kPa).

The alkylation of benzene by linear monoolefins with the requisite conversion, selectivity, and linearity is effected by fluorided silica-aluminas containing a weight ratio of silica to alumina of at least 1:1 (50 weight percent) up to as high as 9:1 (90 weight percent). The stated range is a useful compromise between selectivity and activity. Selectivity of the fluorided silica-aluminas of this invention increases with increasing silica content, which recommends or suggests the use of as high a silica level as possible. However, the activity of the fluorided materials increases initially, appears to pass through a maximum at about a 3:1 ratio of silica:alumina, and then decreases thereafter. Accordingly, although fluorided silica-aluminas can be used throughout the given range, those having a silica to alumina weight ratio between about 65:35 and 85:15 are preferred in the practice of my invention.

Preferred catalysts contain from about 1 up to 6 weight percent fluoride based on volatile-free finished silica-alumina catalyst. Higher fluoride levels may be used but without any substantial incremental benefit. The preferred fluoride level depends on the silica-alumina ratio. For example, for a 75:25 silica:alumina ratio fluoride levels between about 1.5 and 3.5 weight percent are preferred.

An amorphous, cogelled, oil-dropped silica-alumina is preferred for the successful practice of this invention. Other silica-aluminas of the same apparent composition may be used, but generally are inferior to the amorphous, cogelled, oil-dropped product. The oil-drop method of preparing, for example, aluminas is an old, tried and true method dating to U.S. Pat. No. 2,620,314, and therefore will not here be discussed in great detail. The following description will be familiar to one practicing this art and will serve as a general description of the subject method.

The cogelled silica-alumina composition is suitably prepared as spheroidal particles by the well-known oil-drop method. In a preferred method of manufacture, an alumina sol, utilized as an alumina source, is commingled with an acidified water glass solution as a silica source, and the mixture is further commingled with a suitable gelling agent, for example, urea, hexamethylenetetramine (HMT), or mixtures thereof. The mixture is discharged while still below gelation temperature by means of a nozzle or rotating disk, into a hot oil bath maintained at or above gelation temperature. The mixture is dispersed into the hot oil bath as droplets which form into spherical gel particles. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10–16 hours, and then in a suitable alkaline or basic medium for at least 3 to about 10 hours, and finally water washed. Proper gelation of the mixture in the oil bath, as well as subsequent aging of the gel spheres, is not readily accomplished below about 50° C., and at about 100° C., the rapid evolution of the gases tend to rupture and otherwise weaken the spheres. By maintaining sufficient superatmospheric pressure during the forming and aging steps in order to maintain water in the liquid phase, a higher aging temperature may be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature from about 85°–250° C. for a period from about 6 to about 24 hours or more, and then calcined at a temperature from about 300°–760° C. for a period from about 2 to about 12 hours or more.

The fluorided silica-alumina catalysts of this invention are prepared by impregnating the silica-alumina with essentially hydrogen fluoride. This is not to say that HF is the only fluoride source, but rather that the fluoride source is equivalent to HF in affording a fluorided silica-alumina free of additional metals or metallic species and which analytically contains only additional HF. Examples of a suitable fluoride source, in addition to HF, include ammonium fluoride [$NH_4F$], ammonium bifluoride [$NH_4HF_2$], and organic fluorides. When an ammonium fluoride is used $NH_3$ is volatilized during subsequent heating of the fluoride-impregnated silica-alumina. When organic fluorides are used the impregnated silica-alumina is subsequently heated under conditions which oxidize carbon to carbon dioxide and excess hydrogen to water, both of which volatilize to leave the equivalent of an HF-impregnated product.

The preparation of the fluorided silica-alumina catalyst may be performed by a variety of procedures, depending upon the fluoride source, fluoride level sought, and so forth. For example, when an ammonium fluoride is used equal volumes of the silica-alumina and an aqueous solution of the ammonium fluoride containing the desired amount of fluoride are intimately mixed, (e.g., cold rolled) and the mixture subsequently heated to evaporate the water. The resulting fluoride-impregnated product may be dried at 125°–175° C. for several hours, and then calcined at a temperature typically in the 350°–550° C. range for 1–6 hours, depending on the temperature used. For calcination near 400° C. the time generally is about 3 hours. It is found that ammonia is lost from the catalyst when the impregnated material is heated to about 150° C. No significant amounts of fluoride are lost up to a temperature of about 550° C., but fluoride loss is observed at higher temperatures.

When HF is the fluoride source a similar impregnation method may be used, although it also is possible to fluoride the catalyst with a gaseous HF stream. In the latter instance no drying step is necessary and the fluorided material may be calcined directly. Where an organic fluoride is used, the silica-alumina may be impregnated using either a vapor phase or liquid phase source of fluoride. For example, an organic fluoride such as t-butyl fluoride can be impregnated from its solution in a volatile solvent, the solvent subsequently removed by evaporation, the silica-alumina heated to remove the last traces of solvent and then calcined to remove the organic material. This procedure is similar to impregnation using inorganic fluoride but may suffer from fluoride loss on calcination. Alternatively, the t-butyl fluoride may be volatilized, and HF deposited on the silica-alumina via thermal decomposition of the t-butyl fluoride. Fluoride levels can be controlled by gas rate, time and temperature of exposure.

It has been found that the catalysts of my invention are quite sensitive to water. Thus it is desirable that the feedstocks be dried to a level of 1 ppm or less. With increasing feedstock water content the catalysts are found to deactivate. It also is quite desirable to dry the catalyst thoroughly immediately prior to use. This can be successfully done by heating my catalysts in a dry, unreactive gas such as air or nitrogen at a temperature of at least 150° C., but preferably at even higher temperatures. The time needed for adequate drying will depend on such factors as gas flow rate and temperature, but at 300° C. a time from 6 to about 12 hours appears adequate.

Alkylation of benzene by the detergent-range linear monoolefins of this invention may be conducted either as a batch method or in a continuous manner, although the latter is greatly preferred and therefore will be described in some detail. Fluorided silica-alumina catalyst may be used as a packed bed or a fluidized bed. Feedstock to the reaction zone may be passed either upflow or downflow, or even horizontally as in a radial bed reactor. The admixture of benzene and the feedstock containing the total linear monoolefins is introduced at a total benzene:olefin ratio of between 5:1 and 30:1, although usually the ratio is in the range between about 8:1 and 20:1. In one desirable variant olefin may be fed into several discrete points within the reaction zone, and at each zone the benzene:olefin ratio may be greater than 30:1. However, the total benzene:olefin ratio used in the foregoing variant of my invention still will be within the stated range. The total feed mixture, that is, benzene plus feedstock containing linear monoolefins, is passed through the packed bed at a liquid hourly space velocity (LHSV) between about 0.3 and about 6 $hr^{-1}$ depending upon alkylation temperature, how long the catalyst has been used, the ratio of silica to alumina and fluoride level in the catalyst, and so on. The temperature in the reaction zone will be maintained at between about 80 and about 140° C., and pressures generally will vary between about 200 and about 1000 psig (1379–6895 kPa) to ensure a liquid phase alkylation. After passage of the benzene and linear monoolefin feedstock through the reaction zone, the effluent is collected and separated into benzene, which is recycled to the feed end of the reaction zone, paraffin, which is recycled to the dehydrogenation unit, and alkylated benzenes. The alkylated benzenes are usually further separated into the monoalkyl benzenes, used in subsequent sulfonation to prepare the linear alkylbenzene sulfonates, and the oligomers plus polyalkylbenzenes. Since the reaction goes to at least 98% conversion, little unreacted monoolefin is recycled with paraffin.

For alkylation other than detergent alkylation, i.e., in the more general case, the reaction between the alkylatable aromatic compound and the alkylating agent will also be performed generally as described above. Whether the aromatic or the alkylating agent is used in excess depends upon the relative economics of the process, the desirability of the predominance of a particular product, the tendency toward oligomerization of, for example, the olefin, and so forth. However, in general the ratio of the alkylatable aromatic substrate and alkylating agent may range between about 1:20 and 20:1. As stated previously, alkylation temperatures will be in the range of 60°–400° C., although temperatures between 100° and 225° C. are more the norm. Pressures will be adequate to ensure a liquid phase alkylation and usually will be no more than about 500 pounds per square inch, although in the case of lower olefins higher temperatures up to perhaps 2,000 psig may be employed. Whether there is recycling of any of the unreacted components will depend, inter alia, upon the extent of conversion, the economic value of the reactant, the ease with which the unreacted materials are separated from the reaction products, and so forth.

The following examples are illustrative only. They show in some detail how the invention claimed below may be carried out but are not intended to limit the invention in any way.

EXAMPLES

General Procedure. Catalyst was packed in a bed 0.5 inch in diameter and 8 inches long equipped with a sliding thermocouple to survey bed temperature at various depths. The feedstock containing linear monoolefins resulted from dehydrogenation of n-paraffins and had the composition given below.

TABLE 1

| Feedstock Composition (weight percent) | |
|---|---|
| Branched hydrocarbons | 7.9 |
| Unbranched hydrocarbons | 92.1 |

| | Alkenes | Alkanes |
|---|---|---|
| C9 | <0.1 | 0.1 |
| C10 | 0.9 | 7.9 |
| C11 | 4.1 | 31.8 |
| C12 | 3.6 | 24.8 |
| C13 | 2.6 | 15.7 |
| C14 | 0.1 | 0.4 |
| Total | 11.3 | 80.7 |

The feedstock containing the linear monoolefins and benzene at a molar ratio of 15:1 benzene:olefin was fed upflow to the packed bed of catalyst at conditions given in the table. Effluent was analyzed by gas chromatography. Analyses were performed after the reactor had lined out, that is, after equilibrium had been attained.

All silica-alumina catalysts were prepared as 1/16-inch diameter spheres by the oil-dropping method and were fluorided by impregnation with an aqueous solution of ammonium bifluoride containing the desired amount of fluoride. The fluoride-impregnated material was dried at ca. 150° C., then calcined in air at 400° C. for 3 hours, to afford the catalysts listed below. The clay was a montmorillonite clay commercially available as Filtrol 24.

| Catalyst Designation | $SiO_2/Al_2O_3$ | Nominal wt. % F |
|---|---|---|
| A | 90/10 | 0 |
| B | 90/10 | 1.00 |
| C | 90/10 | 1.75 |
| D | 90/10 | 2.50 |
| E | 75/25 | 0 |
| F | 75/25 | 1.75 |
| G | 75/25 | 2.50 |
| H | 75/25 | 3.00 |
| I | 75/25 | 4.00 |
| J | Clay | 0 |

EXAMPLE 1

Reactions of 1-decene. The unfluorided silica-aluminas, (catalysts A and E) montmorillonite clay (catalyst J), and a fluorided silica-alumina (catalyst G) were evaluated for their effect on 1-decene in the absence of benzene by passing a stream of 1-decene in n-decane as a solvent (1:10 weight ratio) over a bed of catalyst at 135° and 150° C. at 500 psig pressure and an LHSV of 2 hr$^{-1}$. Effluent was analyzed for dimer, trimer, cracked products, and methylnonenes. The latter arise from isomerization of and alkyl group migration in 1-decene and can be taken as a measure of the propensity of the catalysts to make non-linear alkylate during alkylation of benzene by 1-decene. Results are given in Table 1.

TABLE 1

| | Conversion of 1-Decene in Absence of Benzene | | | | | | | |
|---|---|---|---|---|---|---|---|---|
| Catalyst | A | | E | | G | | J | |
| Temp, °C. | 150 | 135 | 150 | 135 | 150 | 135 | 150 | 135 |
| % Conversion | 20 | 13 | 31 | 22 | 46 | 32 | 41 | 28 |
| Selectivity, wt. % | | | | | | | | |
| Dimer | 62.5 | 69.2 | 63.3 | 64.3 | 60.1 | 62.6 | 63.2 | 64.2 |
| Trimer | 9.0 | 14.6 | 13.1 | 19.4 | 20.1 | 23.4 | 23.0 | 26.5 |
| Light[a] | 25.0 | 15.3 | 21.3 | 15.1 | 17.2 | 12.6 | 12.0 | 8.3 |
| Ends Me—C9=[b] | 3.5 | 0.9 | 2.3 | 1.2 | 2.6 | 1.4 | 1.8 | 1.0 |
| YIELD, MeC9=[c] | .70 | .12 | .71 | .26 | 1.20 | .45 | .74 | .28 |

[a]Cracked products.
[b]Methylnonenes (branched olefins)
[c]Absolute yield (%) of methylnonenes (conversion x selectivity)

Insofar as conversion is related to catalyst activity, the data show clearly that the fluorided silica-alumina is the most active catalyst, and that fluoridation has a profound effect on activity. However, the selectivity of silica-aluminas to branched olefin production is only slightly changed by fluoridation. Furthermore, branch olefin production is reduced considerably—by about 50% or more—upon reducing the temperature from 150° to 135° C. What these data show rather poignantly is that the extent of branched olefin production is far more sensitive to temperature than to the particular catalyst tested. This is also seen in the last row of the table, where branched olefin yield is seen to decrease by about a third or more in reducing the temperature from 150° to 135° C. Thus, one can confidently extrapolate from these data that decreasing the alkylation temperature of benzene by linear olefins will afford less branched alkylate, regardless of the catalyst.

Another way of looking at these data is to compare the extent of branched olefin production at the same olefin conversion. Insofar as percent olefin conversion can be correlated with the degree of benzene conversion during alkylation, differences in selectivity of branched olefin formation are a measure of expected differences in the non—linearity of alkylate. Table 1 shows that at about 30% 1-decene conversion fluorided silica (G) affords much less branched olefin than its non-fluorided counterpart (E). Presumably this also would hold for catalyst A, although a temperature near 170° C. Would be required for 30% 1-decene conversion.

What is clear and unambiguous from the foregoing data is that fluorided silica-alumina is superior to its non-fluorided counterpart in not effecting branching at conditions giving comparable catalyst activity.

EXAMPLE 2

Alkylation of benzene with 1-decene. Catalyst G was used as a fixed bed to effect the alkylation of benzene by 1-decene, using a feedstock with a benzene:olefin ratio of 25:1, at 500 psig and LHSV of 2 hr$^{-1}$. Table 2 shows results at two temperatures.

TABLE 2

| Alkylation of Benzene with 1-Decene using Catalyst G. | | |
|---|---|---|
| Temperature, °C. | 120 | 100 |
| Olefin Conversion, % | 100 | 100 |
| % Linearity | 95.5 | 97.8 |
| % Methyl Branched | 2.90 | 0.45 |

These data show that temperature has a profound effect on both the extent of linearity and methyl branching in the alkylate. In particular, the extent of methyl branching in the non-linear alkylate decreases from 64% (2.9/4.5) at 120° to 20% (0.45/2.2) at 100° C. We also interpret this data to mean there is a pre-reaction isomerization of 1-decene to form methyl-branched olefins which subsequently alkylate benzene. Once more the data point strongly toward modifying the catalyst to increase alkylation activity so as to permit lower operating temperatures.

EXAMPLE 3

Alkylation of benzene with mixed olefin feedstock; temperature effect on linearity. The feedstock previously described was used as the olefins source for alkylation at a benzene:olefin ration of 25:1 at 500 psig and a LHSV of 2 hr$^{-1}$ using various catalysts, as summarized in Table 3.

TABLE 3

| Catalyst | Effect of Temperature on Linearity of Alkylate | | | | | | | | |
|---|---|---|---|---|---|---|---|---|---|
| | E | | | G | | | J | | |
| % Conversion | 100 | 95 | 70 | 100 | 100 | 100 | 100 | 96 | 72 |
| Temp., °C. | 150 | 135 | 120 | 150 | 135 | 120 | 150 | 135 | 120 |
| % Linearity | 90.2 | 92.1 | 93.4 | 90.0 | 92.5 | 93.6 | 92.1 | 93.5 | 94.9 |

The foregoing data show that the detergent alkylate formed at any given temperature has the same percent linearity, whether or not the silica is fluorided (cf. results of E and G). However, the clay affords a detergent alkylate with somewhat higher linearity, especially at the higher temperature. What distinguishes the fluorided silica-alumina (G) from the other catalysts is its increased activity, for G leads to 100% conversion even at 120° C., whereas the other two catalysts give only about 70% conversion at that temperature. This constitutes a striking example of the advantage of using a fluorided silica-alumina catalyst. More particularly, note that the linearity of alkylate formed at 120° C. using G is the same as that formed at 135° C. using J, but under these conditions G still brings about 100% conversion whereas J does not.

EXAMPLE 4

Effect of fluoride level on silica-alumina catalysts. Alkylation of benzene was performed at 135° C., 500 psig, LHSV of 2 hr$^{-1}$, and a benzene: olefin ratio of 25:1, with the results shown in Table 4. The 75:25 silica-alumina having 2.5% fluoride seemed to have the highest activity, is measured by its having the highest number of hours at 100% conversion. Also note again that the percent linearity is, except for the unfluorided 90:10 silica-alumina, essentially independent of the catalyst.

TABLE 4

| | Effect of Fluoride Level on Silica-alumina Catalyst Performance. | | | | | | | | |
|---|---|---|---|---|---|---|---|---|---|
| Catalyst | A | B | C | D | E | F | G | H | I |
| Hours at 100% Conv. | 18 | 24 | 32 | 44 | 20 | 32 | 48 | 45 | 41 |
| % Linearity | 91.2 | 92.2 | 92.6 | 92.5 | 92.2 | 92.4 | 92.6 | 92.3 | 92.3 |
| % Selectivity | 91.1 | 92.1 | 91.8 | 91.7 | 90.3 | 90.5 | 91.5 | 90.9 | 90.8 |

EXAMPLE 5

Alkylation of benzene with propylene. The alkylation of benzene with propylene may be conducted at 170° C. with a benzene to propylene feed molar ratio of 5. Pressure may be 500 psig and total LHSV=2 hr$^{-1}$. The catalyst of choice is catalyst G containing 2.5 weight percent fluoride. Complete propylene conversion may be expected for about 1 day with a selectivity to cumene of about 80%. Byproducts may be di- and tripropylbenzene as well as oligomer and small quantities of n-propylbenzene.

EXAMPLE 6

Alkylation of benzene with propanol. The alkylation of benzene with propanol may be conducted at 185° C. with a benzene to propanol feed molar ratio of 5. Pressure may be 500 psig and total LHSV=2 hr$^{-1}$. Catalyst G (2.5 weight percent fluoride) may yield complete alcohol conversion for about 1 day with a selectivity to cumene of about 80 percent, Byproducts may be di- and tripropylbenzene as well as olefin oligomer, some diisopropylether, and small quantities of n-propylbenzene.

EXAMPLE 7

Alkylation with long-chain olefins. A feedstock of commercially available linear alpha-olefins, containing 35 weight percent C20, 45% C22, and 20% C24 monoolefins, and 25 molar proportions benzene was reacted at 500 psig, 2.0 LHSV, and 150° C. using catalyst G. Complete olefin conversion was maintained for 26 hours to afford monoalkylbenzenes with a selectivity of 90% and a linearity of 89%.

What is claimed is:

1. A process of alkylating an alkylatable aromatic compound with an alkylating agent comprising reading in the liquid phase the alkylatable aromatic compound with the alkylating agent under alkylating conditions in the presence of an alkylation catalyst comprising a fluorided silica-alumina containing from about 1 to about 6 weight percent fluorine.

2. The process of claim 1 where the alkylatable aromatic compound is selected from the group consisting of benzene, naphthalene, anthracene, phenanthrene, and benzene, naphthalene, anthracene, and phenanthrene bearing at least one substituent selected from the group consisting of alkyl, hydroxy, alkoxy, phenyl, and phenylalkyl, where each alkyl and alkoxy group contains from 1 up to about 20 carbon atoms.

3. The process of claim 2 where the alkylatable aromatic compound is benzene.

4. The process of claim 2 where the alkylatable aromatic compound is toluene.

5. The process of claim 2 where the alkylatable aromatic compound is a hydroxybenzene.

6. The process of claim 2 where the alkylatable aromatic compound is an alkoxybenzene.

7. The process of claim 2 where the alkylating agent is an olefin, an alcohol, or an alkyl halide containing from 1 up to about 24 carbon atoms.

8. The process of claim 1 where alkylating conditions include a temperature from about 60° up to about 400° C.

9. The process of claim 8 where the temperature is from about 100° up to about 225° C.

10. The process of claim 1 where the catalyst has a silica to alumina weight ratio of from 65:35 to about 85:15.

11. The process of claim 1 where the catalyst contains from 1.5 to about 3.5 weight percent fluoride.

* * * * *